US00PP27527P3

(12) United States Plant Patent
O'Connell

(10) Patent No.: US PP27,527 P3
(45) Date of Patent: Jan. 3, 2017

(54) ***ECHEVERIA* PLANT NAMED 'CUBIC FROST'**

(50) Latin Name: ***Echeveria* hybrid**
Varietal Denomination: Cubic Frost

(71) Applicant: Renee O'Connell, Escondido, CA (US)

(72) Inventor: Renee O'Connell, Escondido, CA (US)

(73) Assignee: Altman Plants, Vista, CA (US)

( * ) Notice: Subject to any disclaimer, the term of this patent is extended or adjusted under 35 U.S.C. 154(b) by 77 days.

(21) Appl. No.: 14/544,913

(22) Filed: Mar. 6, 2015

(65) Prior Publication Data

US 2016/0270277 P1 Sep. 15, 2016

(51) Int. Cl.
*A01H 5/12* (2006.01)

(52) U.S. Cl.
USPC ..... Plt./373

(58) Field of Classification Search
USPC ..... Plt./373
See application file for complete search history.

*Primary Examiner* — Susan McCormick Ewoldt

(57) ABSTRACT

A new and distinct *Echeveria* cultivar named 'Cubic Frost' is disclosed, characterized by concentric, geometric rosettes, comprised of many uplifted, slightly undulate, slightly tubular, lilac to lilac pink leaves. The new cultivar *Echeveria* 'Cubic Frost' exhibits robust growth, enabling shorter production intervals. *Echeveria* 'Cubic Frost' is freely offsetting, enhancing propagation intervals, as well as creating attractive clusters. *Echeveria* 'Cubic Frost' prolifically produces plantlets from leaf cuttings, further enhancing propagation in the commercial nursery. The new culitvar 'Cubic Frost' is freely flowering, producing a larger flower with an unusual shape. The new variety is an *Echeveria*, part of the Crassulaceae complex that includes *Pachyphytum, Graptopetalum, Sedum, Crassula* and others. *Echeveria* is a popular genus, typically produced as container plants or landscape plants. Currently, there is a growing use of *Echeveria* for artistic creations such as wedding bouquets, table centerpieces and other ornamental uses for social occasions.

4 Drawing Sheets

Latin name of the genus and species: *Echeveria* hybrid. Variety denomination: 'CUBIC FROST'.

BACKGROUND OF THE INVENTION

The new *Echeveria* cultivar is the product of a planned breeding program. The new variety originated from a cross pollination of the proprietary, unpatented, seed parent, *Echeveria* 'Doppler' with the pollen parent, an unpatented, proprietary variety of *Echeveria* referred to as 'R-21'. The pollination was made during April of 2011 at a commercial greenhouse in Vista, Calif.

'Cubic Frost' was discovered by the inventor, Renee O'Connell, in September of 2011, in Vista, Calif. at a commercial greenhouse in Vista, Calif.

Asexual reproduction of the new cultivar 'Cubic Frost' was first performed in Vista, Calif., at a commercial greenhouse by vegetative cuttings in March of 2012. 'Cubic Frost' has since produced multiple generations and has shown that the unique features of this cultivar are stable and reproduced true to type.

SUMMARY OF THE INVENTION

The cultivar 'CUBIC FROST' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CUBIC FROST' These characteristics in combination distinguish 'CUBIC FROST' as a new and distinct *Echeveria* cultivar:

1. Exhibits a concentric, geometric rosette, comprised of many uplifted, slightly undulate, slightly tubular lilac to lilac pink leaves, a combination of characteristics not displayed by comparable *Echeveria* varieties.
2. Exhibits robust growth, enabling shorter production intervals, a characteristic not seen in many other comparable *Echeveria* varieties.
3. Freely offsetting, enhancing propagation, in comparison to many other *Echeveria* varieties.
4. Prolifically produces plantlets from leaf cuttings, a characteristic not found in many other *Echeveria* varieties.
5. Free flowering, and displays larger, unusually shaped flowers, not observed in many comparable *Echeveria* varieties.

Plants of the new cultivar 'CUBIC FROST' are similar to plants of the seed parent, *Echeveria* 'Doppler' in most horticultural characteristics, however, plants of the new cultivar 'CUBIC FROST' differ in the following;

1. Exhibit a lilac to pink lilac coloration, seed parent is mainly grey-blue with some pink.
2. Freely offsets, enhancing propagation and quickly forming attractive clusters, not observed in the seed parent.
3. Prolifically produces plantlets from leaf cuttings, further enhancing propagation, whereas the seed parent is far less prolific in producing plantlets from leaf cuttings.

4. Exhibits more disease resistance than the seed parent, in particular to the pathogen, *Fusarium*, a common *Echeveria* disease.

Plants of the new cultivar 'CUBIC FROST' are similar to plants of the pollen parent, *Echeveria* 'R-21' in most horticultural characteristics, however, plants of the new cultivar 'CUBIC FROST' differs in the following;

1. More concentric, geometric rosette
2. Freely offsets, enhancing production and creating an attractive cluster, whereas the pollen parent offsets only occasionally.
3. Prolifically produces plantlets from leaf cuttings, whereas the pollen parent only occasionally produces a plantlet from a leaf cutting.

COMMERCIAL COMPARISON

Plants of the new cultivar 'CUBIC FROST' are comparable to the unpatented, commercial variety *Graptoveria* 'Debbi'. The two varieties are similar in most horticultural characteristics; however, the new variety 'CUBIC FROST' differs in the following:

1. Forms a more concentric, geometric rosette than *Graptoveria* 'Debbi', producing a more aesthetic rosette plant form.
2. Offset more profusely than *Graptoveria* 'Debbi', enhancing propagation, and producing a morphologically aesthetic cluster.
3. Produces larger, more unusually shaped flowers than does *Graptoveria* 'Debbi'.

Plants of the new cultivar 'CUBIC FROST' can also be comparable to the unpatented commercial variety *Echeveria* 'Topsy Turvy'. The two *Echeveria* varieties are similar in most horticultural characteristics; however, the new variety 'CUBIC FROST' differs in the following:

1. Exhibit a very concentric, geometric rosette, as compared to the looser, longer-leaved rosette exhibited by *Echeveria* 'Topsy Turvy'.
2. Displays a lilac coloration of the leaves; *Echeveria* 'Topsy 'Turvy' has greyed-green foliage.
3. Freely offsets, forming attractive clusters at an early age, as compared to the *Echeveria* plant 'Topsy Turvy', which offsets occasionally, but not as freely, nor at as young an age.
4. Has a faster rate of growth than *Echeveria* 'Topsy Turvy', and that characteristic, combined with the free offsetting of the new cultivar 'Cubic Frost', enhances production intervals and propagation intervals, as compared with *Echeveria* 'Topsy Turvy'.

BRIEF DESCRIPTION OF THE PHOTOGRAPHS

The accompanying photograph in FIG. 1 illustrates in full color a freely offsetting plant of *Echeveria* 'Cubic Frost', grown in a greenhouse in Vista, Calif.

Figure 1:
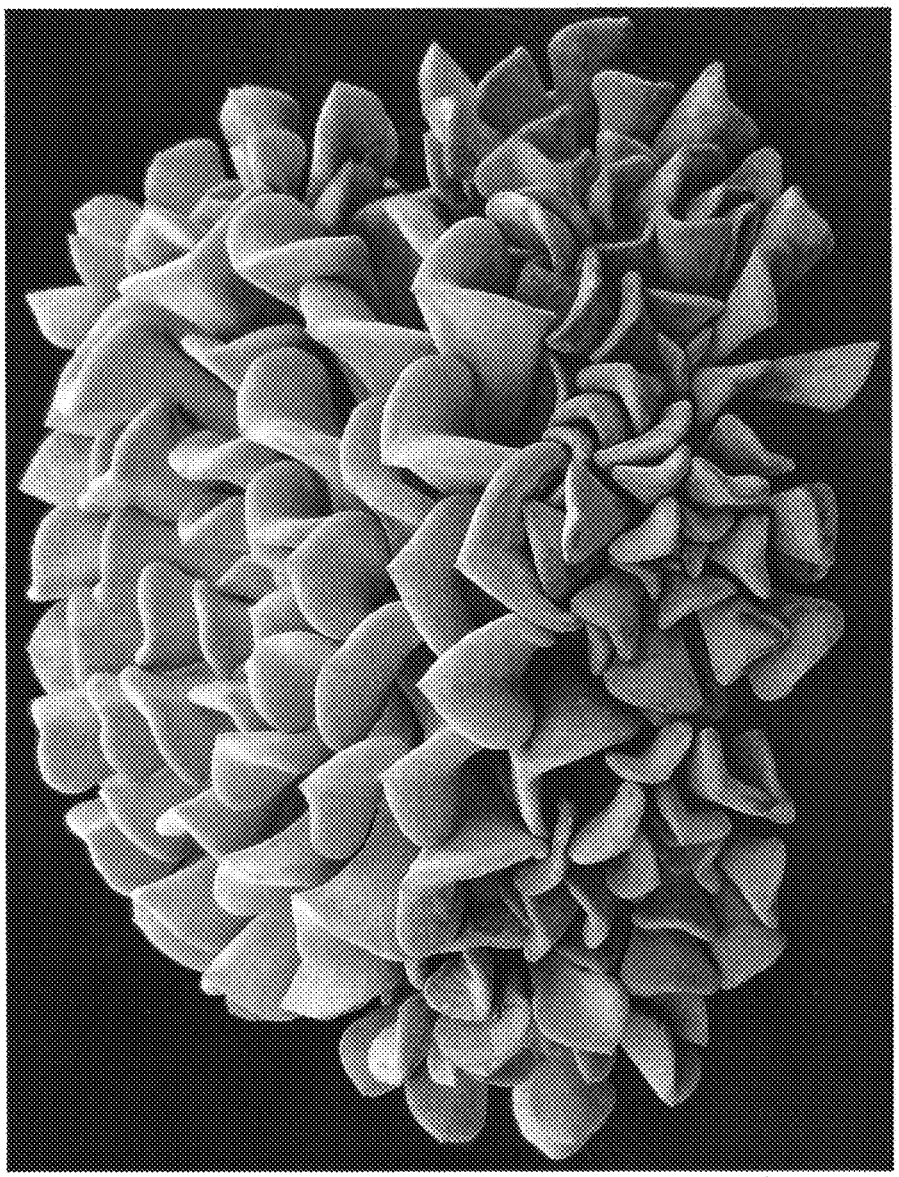
Figure 2:
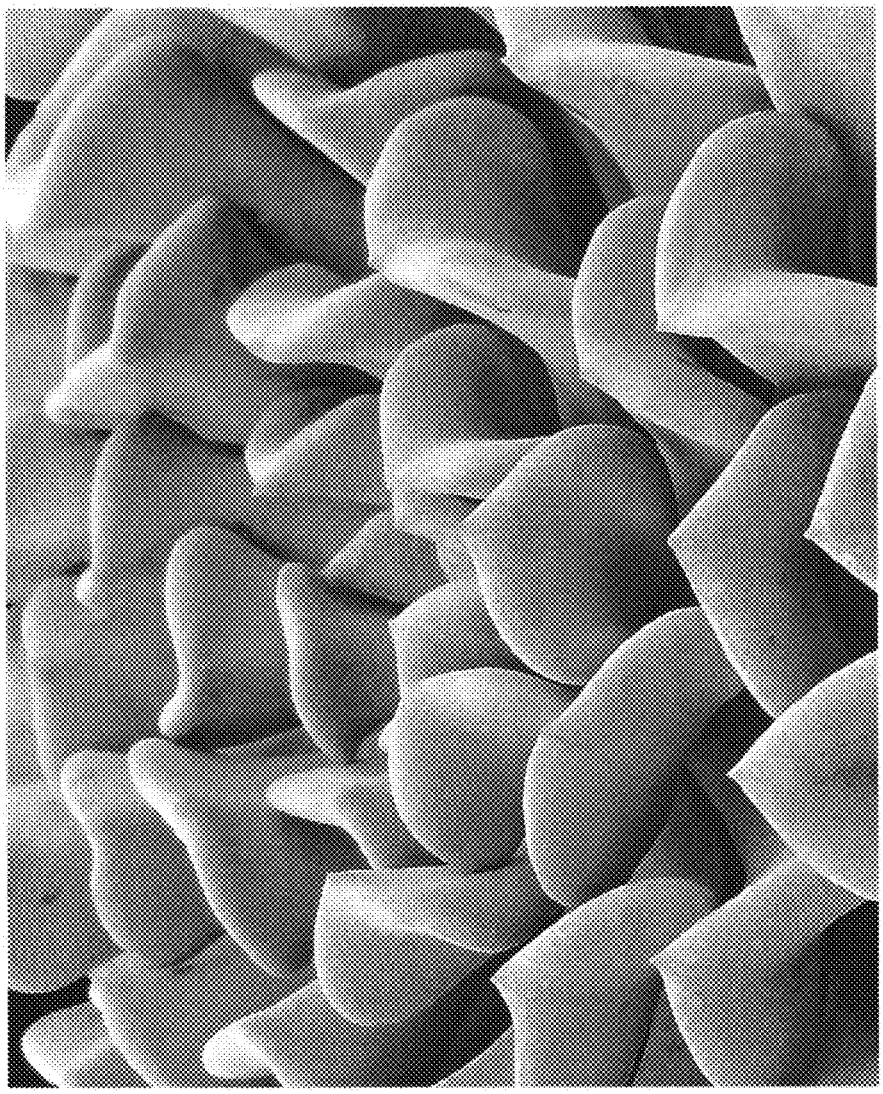
FIG. 2 illustrates in full color a close up of the rosette of the new cultivar 'Cubic Frost', grown in a greenhouse in Vista, Calif.
Figure 3:
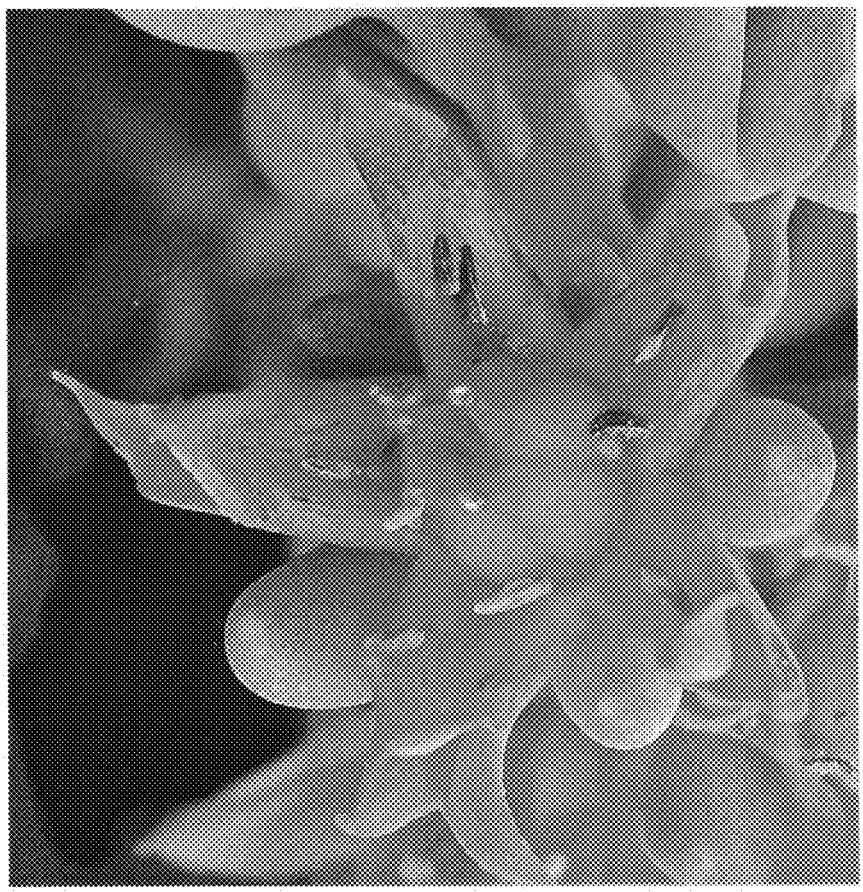
FIG. 3 illustrates in full color a close up of the unusually shaped flower of the new cultivar 'Cubic Frost', grown in a greenhouse in Vista, Calif.
Figure 4:
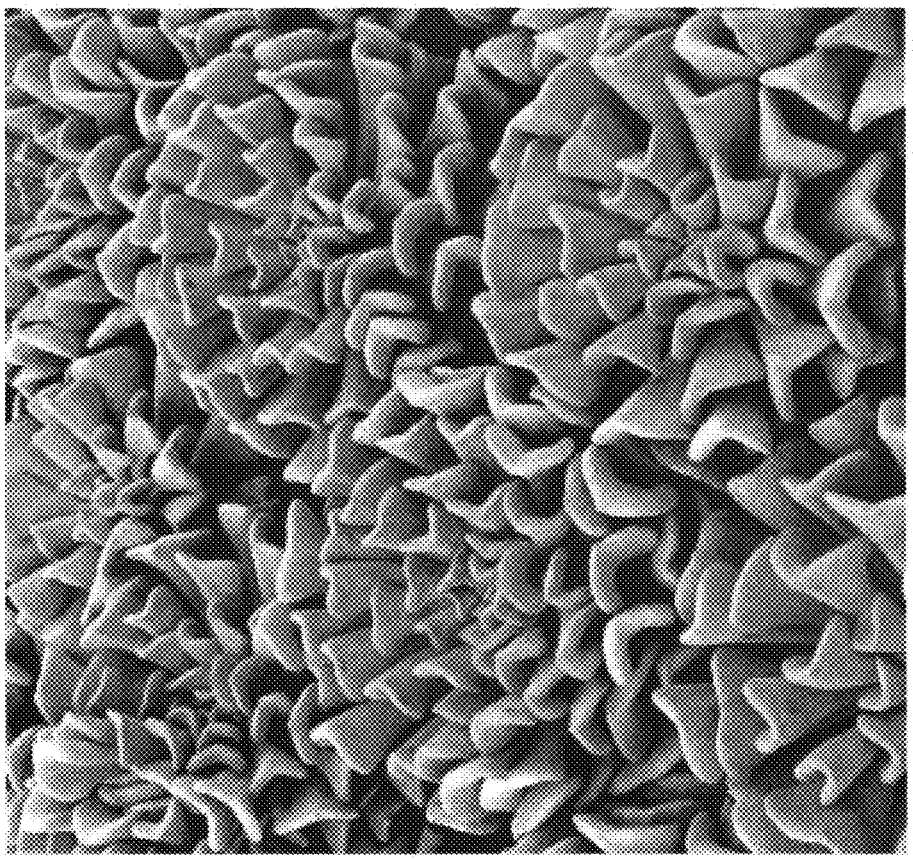
FIG. 4 illustrates in full color a group planting of the new cultivar 'Cubic Frost', at a greenhouse in Vista, Calif.

The photographs were taken using conventional techniques and although colors may appear different from actual colors due to light reflectance it is as accurate as possible by conventional photographic techniques.

DETAILED BOTANICAL DESCRIPTION

In the following description, color references are made to the Pantone Process Color System Guide, Pantone CYMK, 2014, except where general terms of ordinary dictionary significance are used. The following observations and measurements describe 'Cubic Frost' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Echeveria* hybrid 'CUBIC FROST'.

PROPAGATION

Type of propagation typically used: Terminal vegetative divisions, offsets, leaf cuttings.

Time to initiate roots: About 14 days at approximately 22° C.

Root description: Fibrous.

PLANT

Age of plant described: Approximately 4 months from cutting.

Container size of the plant described: 16 cm.

Growth habit: Densely rosulate, sessile.

Height: Approximately 7.5 cm to top of highest leaf. Approximately 57 cm to top of highest inflorescence.

Plant spread: 17.5 cm.

Growth rate: Moderately fast.

Branching characteristics: Freely offsetting.

FOLIAGE

Leaf:

*Arrangement*.—Rosulate.

*Average length*.—Approximately 5.7 cm.

*Longest length*.—Approximately 7.3 cm.

*Widest width*.—Approximately 3.6 cm.

*Width at base*.—1.15 cm.

*Shape of blade*.—Spathulate, convex above, concave below.

*Apex*.—Mucronate.

*Base*.—Cuneate.

*Margin*.—Rounded.

*Texture of top surface*.—Glabrous, glaucous.

*Texture of bottom surface*.—Glabrous, glaucous.

*Quantity of leaves per plant*.—Approximately 63.

*Color*.—Young foliage upper side, middle of leaf: Near P 100-11 U Pantone. Young foliage, upper side, near stem: Near P 160-5 U Pantone. Young foliage upper side, marginal blush: Near P 83-13 U Pantone. Young foliage, under side: Near P 95-12 U Pantone. Young foliage underside, near stem: Near P 160-5 U Pantone. Mature foliage, upper side: Near P 129-11 U Pantone. Mature foliage, upper side, near stem: Near P159-3 U Pantone. Mature foliage, apical tip: Near P 86-8 U Pantone. Mature foliage, under side:

Near P 129-10 U Pantone. Mature foliage, under side, near stem: Near P 159-2 U Pantone. Venation: There is no visual appearance of venation.

FLOWER

Natural flowering season: Spring, Summer.

Inflorescence type and habit: Lateral, bifurcate.

Rate of flower opening: 1 flower opens every 2-3 days, depending upon ambient conditions.

Flower longevity on plant: 2-3 days, depending upon ambient conditions.

Quantity of flowers: 29.

*Total inflorescence size*.—Height: Approximately 50.5 cm. Width: Approximately 16 cm.

*Corolla*.—

*Arrangement*.—5-merous, but with double petals, the outer petals spreading to recurved.

*Size*.—Length: Approximately 1.1 cm. Width: Approximately 1.9 cm at widest point. Lobe Length: Approximately 1.1 mm. Lobe width: Approximately 0.4 mm. Margin: Entire. Shape: Irregularly ensiform (monstrous). Apex: Acute. Texture: Glabrous.

*Petal color: when opening*.—Petal color, outer surface: Near P 55-5 U Pantone. Petal color, outside tip: P 55-13 U Pantone.

*Petal color, fully opened*.—Outer surface, near base: Near P 62-5 U Pantone. Inner surface, apex: Near P 55-15 U Pantone. Inner surface, middle of petal: Near P 24-4 U Pantone.

*Color changes when aging*.—Near P 55-6 U Pantone.

*Bud:* (*near opening*).—Shape: Conical. Length: Approximately 1.5 cm. Diameter: Approximately 0.9 cm. Color, Apex of Bud: Near P 97-9 U Pantone. Color, Base of Bud: Near P 57-12 U Pantone.

*Sepals*.—Length of sepal: Approximately 0.6 cm long. Width of sepal: Approximately 0.3 cm at widest point. Color, where glaucous layer removed: Near P 178-12 U Pantone. Color, with glaucous layer intact: Near P 86-3 U Pantone.

*Pedicels*.—Length: Approximately 1.4 cm. Width: Approximately 0.3 cm. Aspect: Slightly spreading. Color: Near P 176-6 U Pantone.

*Fragrance*.—None detected.

REPRODUCTIVE ORGANS

Stamens: (Androecium).

*Number*.—Average 10.

*Filament length*.—Approximately 0.7 cm.

*Filament color*.—Near P 55-7 U Pantone.

*Anther length*.—0.3 cm.

*Anther color*.—Before dehiscence, near P 7-13 U. Pantone, with striations of P 48-15 U Pantone.

*Anther shape*.—Elliptic.

*Pollen color*.—Near P 4-4 U Pantone.

Pistil: (Gymnoecium).

*Number*.—Average 5.

*Length*.—Approximately 1.05 cm.

*Style color*.—Near P 30-1 U Pantone.

*Style length*.—Approximately 0.6 cm.

*Stigma*.—Shape: Oblong. Color: Near P 38-15 U Pantone. Ovary Color: Near P 106-3 U Pantone.

OTHER CHARACTERISTICS

Fruits and seeds: No outstanding differences noted from typical fruits and seeds.

Temperature tolerance: Tolerates temperatures from approximately −2 C to 32 C.

Disease/pest resistance: More resistance to the pathogen known as *Fusarium*, a typical disease of *Echeveria*, has been observed. Neither resistance nor susceptibility to normal pests of *Echeveria*, which include thrips and aphid.

Drought tolerance: Tolerates at least 3 weeks of high temperatures without supplemental water, showing no serious damage to plant.

What is claimed is:

1. A new and distinct cultivar of *Echeveria* plant named 'CUBIC FROST' as herein illustrated and described.

* * * * *